US00PP26300P3

(12) United States Plant Patent
Lombard

(10) Patent No.: US PP26,300 P3
(45) Date of Patent: Jan. 12, 2016

(54) GRAPE PLANT NAMED 'TAWNY SEEDLESS'

(50) Latin Name: *Vitis vinifera*
Varietal Denomination: Tawny Seedless

(71) Applicant: Lombardi Genetics (Pty) Ltd, Paarl (ZA)

(72) Inventor: Andre Benjamin Lombard, Mokopane (ZA)

(73) Assignee: LOMBARDI GENETICS (PTY) LTD, Paarl (ZA)

( * ) Notice: Subject to any disclaimer, the term of this patent is extended or adjusted under 35 U.S.C. 154(b) by 125 days.

(21) Appl. No.: 13/999,778

(22) Filed: Mar. 20, 2014

(65) Prior Publication Data

US 2015/0271971 P1 Sep. 24, 2015

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para
(74) *Attorney, Agent, or Firm* — Hahn Loeser & Parks LLP

(57) ABSTRACT

A new and distinct cultivar of grapevine (*Vitis vinifera*) plant named 'Tawny Seedless', characterized by its strong plant growth vigor, high fertility, high resistance to rain, exceptional post-harvest shelf life, low requirement for labor, large fruit size with round shape, firm fruit with good flavor. This combination results in a higher quality fruit with a later availability than other varieties.

7 Drawing Sheets

Latin name of the family, genus, and species:
Family—Vitaceae.
Genus—*Vitis.*
Species—*vinifera.*
Variety denomination: The new grape plant claimed is of the variety denominated 'Tawny Seedless'.

BACKGROUND OF THE INVENTION

The present invention relates to a new and distinct *Vitis vinifera* (grapevine) variety, which has been given the variety denomination of 'Tawny Seedless'. The new variety 'Tawny Seedless' shows distinctive traits such as high productivity, good flavor, prolonged post-harvest shelf life and robust resistance to rain.

The new variety 'Tawny Seedless' is the result of a grapevine breeding program that was commenced in the summer of 2002 in South Africa. The female (seed) parent 'Red Globe' and male (pollen) parent 'Flame Seedless' were crossed with the hope that they would contribute to desired characteristics of a new variety better than existing red and black seedless varieties. The seedlings from the cross were obtained and 'Tawny Seedless' was selected as a promising early ripening red seedless variety.

SUMMARY OF THE INVENTION

Many favorable characteristics of the new variety have been repeatedly observed and can be used to distinguish 'Tawny Seedless' as a new and distinct variety of *Vitis vinifera*, among which the following are considered the most favorable:

1. The variety is extremely labor friendly, needing very little manual work on the clusters.
2. The variety is highly fertile and fruitful.
3. The variety has natural large berries which require low concentrations of gibberellic acid to enhance berry size.

4. The variety colors well and needs very low concentrations of Ethepon to enhance color development.
5. The variety produces berries that are very crispy.
6. The variety has an exceptional shelf-life for a seedless variety.
7. The variety is highly resistant to rain.

Plants of the new variety have maintained the distinguishing characteristics throughout successive asexual propagation.

The new variety 'Tawny Seedless' originated from a hand pollinated crossing between the female (seed) parent 'Red Globe' (*Vitis vinifera*) and the male (pollen) parent 'Flame Seedless' (*Vitis vinifera*) in September 2002 in Mokopane District, Limpopo, South Africa.

The female parent 'Red Globe' is a multiple cross of, among others, grapevine varieties known as 'Red Emperor', 'Hunisa' and 'Nocera'. The male parent 'Flame Seedless' is a multiple cross of, among others, grapevine varieties known as 'Cardinal', 'Sultanin', 'Malaga' and 'Muscat d'Alexandria'.

Seeds produced by this controlled hybridization were germinated in a hothouse on a farm in Mokopane District, Limpopo, South Africa. From the seedlings produced from the seeds, seedling L2004/01 was selected for its excellent plant characteristics and was given the cultivar denomination 'Tawny Seedless'. Grapes from this selection were evaluated for its viticultural characteristics, as well as post-harvest storage and market acceptance. Particularly, selection criteria include seedlessness, fertility, labor requirement, berry size, color development, taste profile and crispiness, ability to withstand rain at harvest time, shelf-life and expected market response and acceptance.

Three generations of 'Tawny seedless' were propagated asexually. During August 2004, the original selection was propagated asexually from hardwood cuttings on own root on the above noted location. Twenty plants were established. These plants were monitored and no mutations were observed. During August 2009, a second propagation was performed and 200 plants were established in a commercial vineyard. During 2013, the third propagation was performed in a commercial vineyard.

All the plants propagated asexually from the original 'Tawny Seedless' selection are genetically stable, producing red seedless berries with a white, crispy flesh and white juice. Particularly, the berries have a neutral yet sweet taste. The skin of the berries is red and tough but does not affect eating quality negatively. It dissolves with the flesh. The vines show a high fertility and often produce two clusters per shoot. The clusters are large, rather straggly and resemble the clusters of 'Red Globe' after set until about 10 mm berry size. The vines are very vigorous, stronger than 'Flame Seedless'. Canes are greyish in color and show a distinctive grooving. The shoots produce fairly strong tendrils and the leaves are not similar to 'Flame Seedless'. It shows no rose coloring of the nerves at the petiolar sinus. The berries have a round shape with a natural average diameter of 18 mm. Bunches are straggly and seldom require thinning. With a low concentration of gibberelic acid sizing, the berries can reach an average size of 23 mm in diameter. The berries color well and the use of coloring enhancers like Ethepon is optional. The berries are highly resistant to rain and can hang well on the vine. Optimal eating quality is reached at a minimum sugar level of 16° B. In commercial vineyards with a normal spray programme, no fungal disease problems are observed.

The clusters and berries of 'Tawny Seedless' resemble those of 'Red Globe'. 'Tawny Seedless' is more fertile than both its parents and is similar in vigour or stronger than the most vigorous varieties such as 'Autumn Royal' or 'Crimson Seedless'. Too much vigour can be a problem on fertile soils with vigorous rootstocks like 'Ramsey'. The berries of 'Tawny Seedless' are larger and more even in size than 'Flame Seedless', but smaller than 'Red Globe'. The berries of 'Tawny Seedless' show a much higher resistance to cracking after rain than 'Flame Seedless'. During the packing process both 'Red Globe' and 'Flame Seedless' exhibit tendencies to micro-crack resulting in waste berries and rotten bunches. 'Tawny Seedless' does not have this problem and thus have an outstanding post-harvest shelf life.

BRIEF DESCRIPTION OF THE DRAWINGS

The accompanying photographic illustration shows typical specimens in full color of the foliage and fruit of the new variety 'Tawny Seedless'. The colors are as nearly true as is reasonably possible in a color representation of this type.

Figure 1:
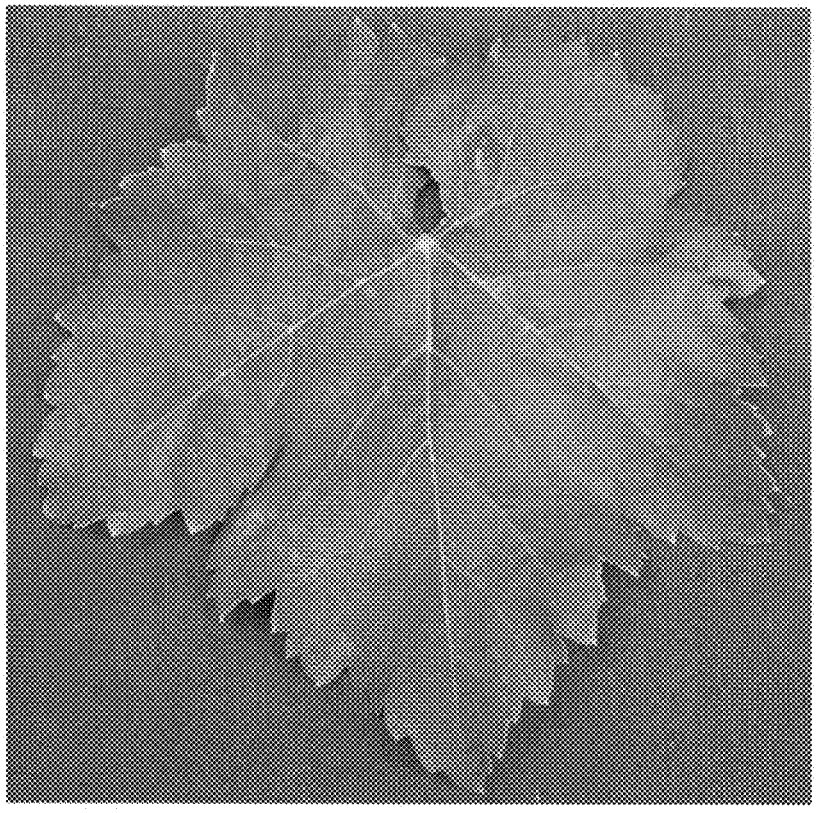
FIG. 1 is a photograph showing the front view of a 'Tawny Seedless' leaf.
Figure 2:
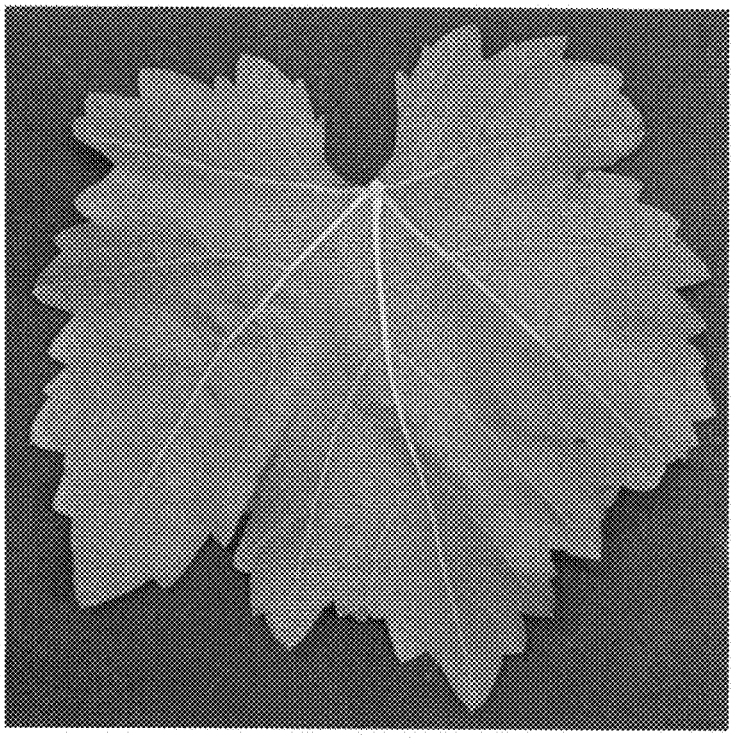
FIG. 2 is a photograph showing the rear view of a 'Tawny Seedless' leaf.
Figure 3:
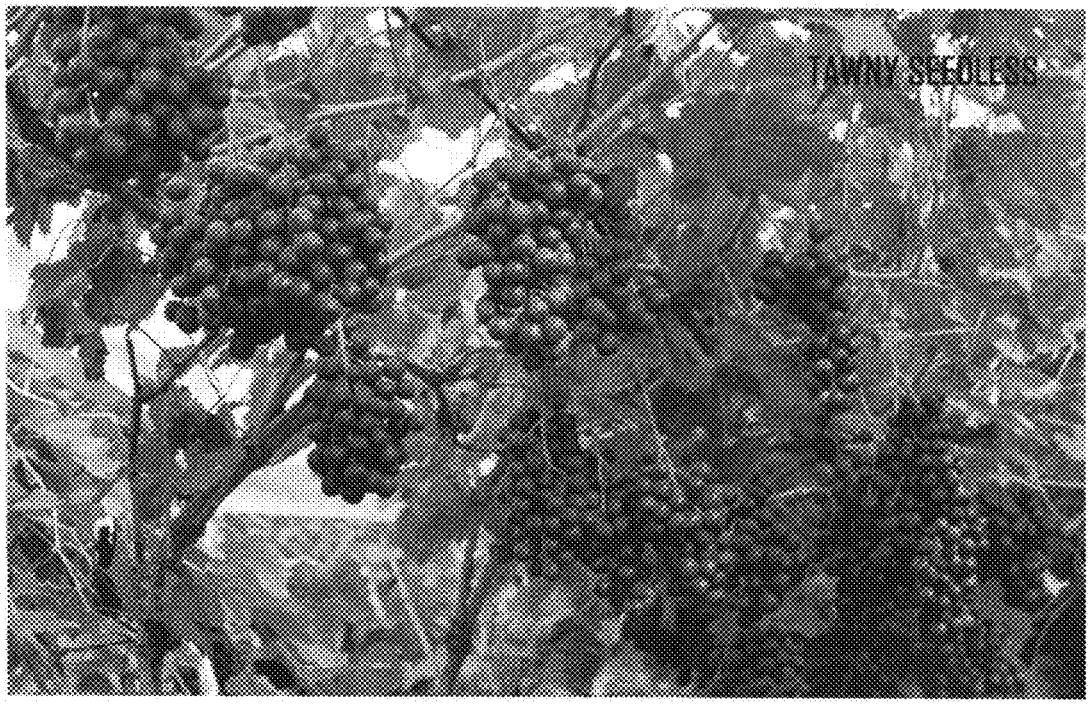
FIG. 3 is a photograph showing trunk, canes, leaves and fruit of a 'Tawny Seedless' plant.
Figure 4:
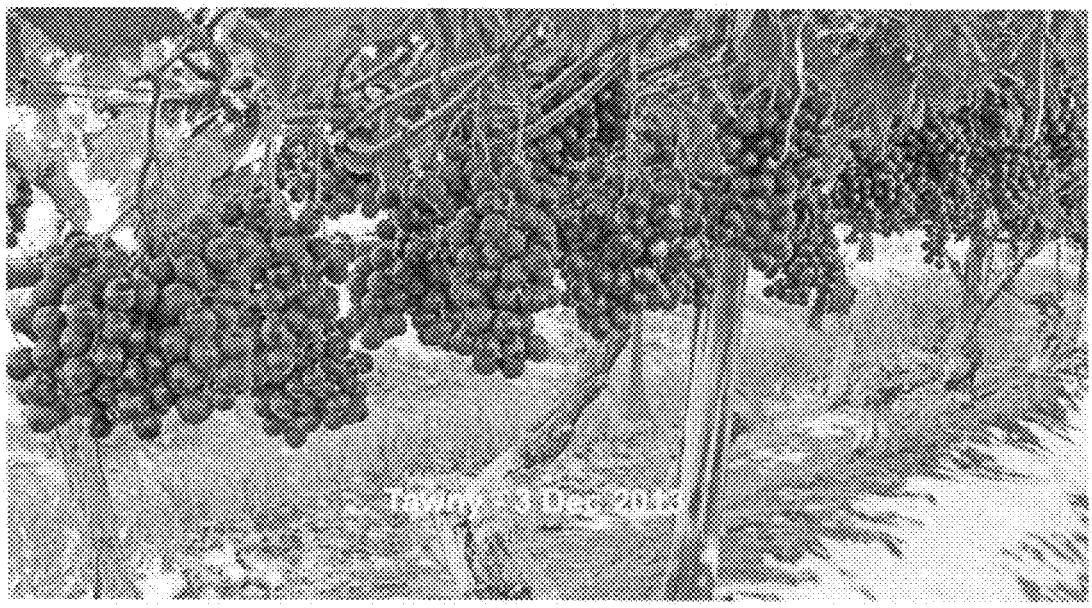
FIG. 4 is a photograph showing multiple fruit clusters of 'Tawny Seedless'.
Figure 5:
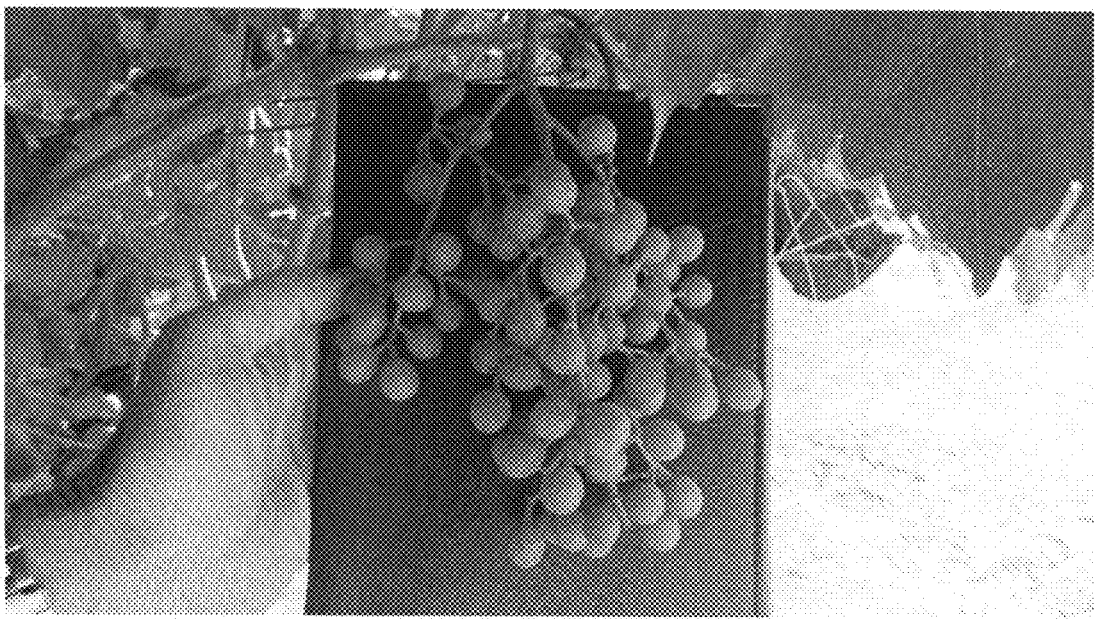
FIG. 5 is a photograph showing the green fruit of 'Tawny Seedless'.
Figure 6:
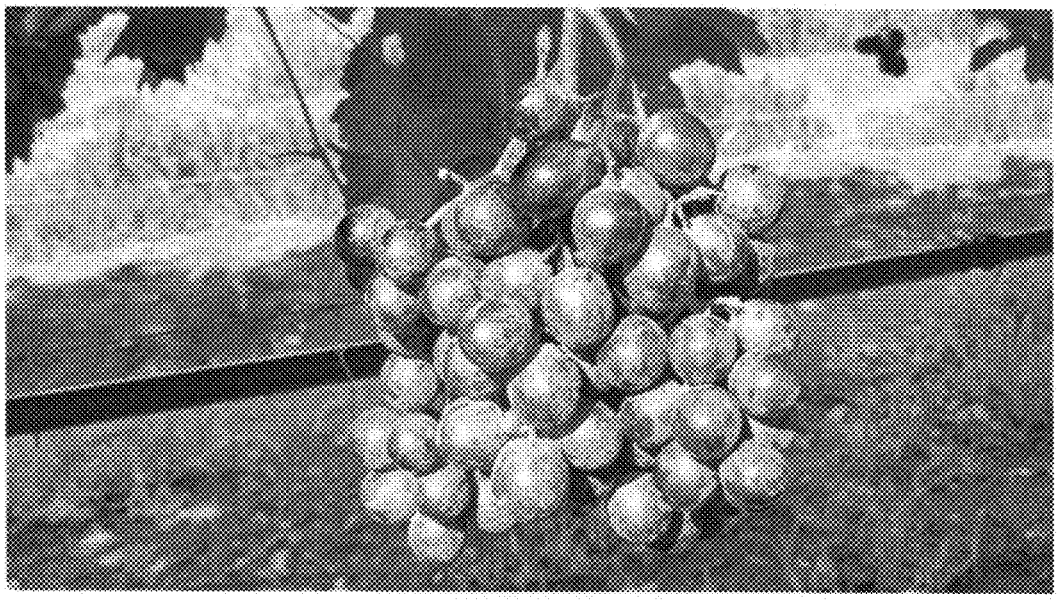
FIG. 6 is a photograph showing a close up of a typical fruit cluster of 'Tawny Seedless'.
Figure 7:
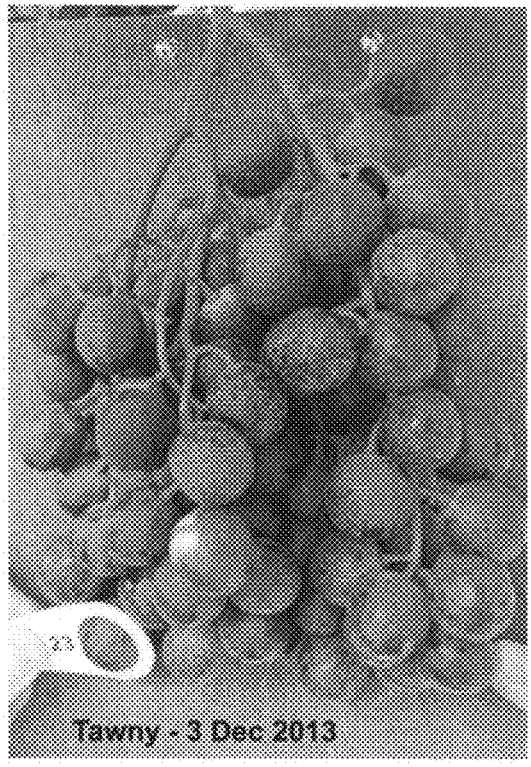
FIG. 7 is a photograph showing the shape and diameter measurement of the fruit of 'Tawny Seedless'.

The colors in the photographs are as close as possible with the photographic and printing technology utilized. The color values cited in the detailed botanical description accurately describe the colors of the new grape.

DETAILED BOTANICAL DESCRIPTION

The following detailed description sets forth the distinctive characteristics of 'Tawny Seedless'. The data which defines these characteristics was collected from asexual reproductions of the original selection. Dimensions, sizes, colors, and other characteristics are approximations and averages set forth as accurately as possible. The plant history was taken on plants approximately 9 years of age, and the descriptions relate to plants grown in the field in Mokopane District, Limpopo, South Africa. Descriptions of fruit characteristics were made on fruit grown in Mokopane District, Limpopo, South Africa. Color designations are from the Pantone® Matching System (PMS) color guide.

Classification:

*a. Family*—Vitaceae.
*b. Genus—Vitis.*
*c. Species—vinifera.*
*d. Common name*—Grapevine.

Parentage:

*Female parent*.—'Red Globe'.
*Male parent*.—'Flame Seedless'.

Market class: Table grapes for human consumption.

VINE

General:

*Size*.—3 m×1, 6 m spacing on a double gable trellising system.
*Vigor*.—Very Strong.
*Productivity*.—High.
*Hardiness*.—Excellent.
*Rootstock*.—Ramsey.

TENDRILS

General:

*Number*.—The discontinuous 2-0-2 configuration (Two-Zero-Two), typical of *Vitis vinefera*.
*Length*.—25 cm.
*Diameter*.—2-4 mm at the base.
*Texture*.—Smooth.
*Color*.—Green (PMS 376).

WOODY SHOOT

Trunk:

*Trunk circumference*.—10 cm at 0.5 meter height.
*Shape*.—Round.
*Surface texture*.—Rough.
*Outer bark color*.—Brown Grey PMS 465.

Canes:

*Shape of canes in cross section*.—Elliptical/Oval.
*Internode length*.—10-12 cm.
*Width at node*.—1 cm.
*Surface*.—Grooved.
*Main color*.—Medium brown (PMS 143).
*Fall color*.—Medium brown (PMS 143).
*Lenticels*.—Rare.
*Erect hairs on nodes*.—Absent.
*Erect hairs on internodes*.—Absent.
*Growth of auxiliary shoots*.—Yes.
*Shape of nodes in cross section*.—Oval/Elliptical.

*Number.*—30 per vines.
*Length.*—1.2 m.
*Diameter.*—10-12 mm.
*Internode length.*—10-12 cm.
*Color.*—Medium Brown (PMS 143).

Buds:
*Date of bud break.*—15 August.
*Average number of buds on a mature cane.*—40.
*Position of buds.*—Spurs.
*Shape.*—Large, dome shaped and ovoid.
*Length.*—12 mm.
*Width.*—7 mm.
*Color.*—Green (PMS 376).
*Texture.*—Smooth.

LEAVES

Mature leaves:
*Average leaf length.*—16 cm for mature leave.
*Average leaf width.*—16 cm.
*Shape.*—Cuneiform or shield shaped (Pentagonal).
*Anthocyanin coloration of main veins on lower leaf surface.*—None.
*Mature leaf profile.*—Flat.
*Blistering surface of blade upper surface.*—Smooth/weak.
*Leaf blade tip.*—Large, pointed and angular.
*Margins.*—Convex toothed.
*Apex.*—Angular.
*Base.*—Typical lyre.
*Thickness (of leaf).*—0.5 mm.
*Undulation of blade between main and lateral veins.*—Mild undulation.
*Shape of teeth.*—Convex (BB).
*Length of teeth.*—5 mm. (Medium).
*Ratio length/width of teeth.*—1:1 (Medium).
*General shape of petiole sinus.*—Typical lyre.
*Tooth at petiole sinus.*—Sharp (RR).
*Petiole sinus limited by veins.*—Absent.
*Shape of upper lateral sinus.*—Deep, cartel folding over.
*Prostrate hairs between veins on lower surface of blade.*—Absent.
*Erect hairs between veins on lower surface of blade.*—Absent.
*Prostrate hairs on main veins on lower surface of blade.*—Absent.

Upper surface:
*Summer color.*—Dark green PMS 364.
*Autumn color.*—Yellow PMS 395.
*Surface texture.*—Smooth to slightly uneven.
*Surface appearance.*—Smooth to slightly uneven.
*Goffering of blade.*—Light to not-distinctive.

Lower surface:
*Summer color.*—Green PMS 377.
*Autumn color.*—Yellow PMS394.
*Anthocyanin coloration of main veins on lower leaf surface.*—Absent.
*Glossiness.*—None.
*Pubescence.*—Absent to very sparse.
*Surface texture.*—Smooth to slightly uneven.
*Surface appearance.*—Smooth to slightly uneven.

Petiole:
*Length of petiole.*—10-12 cm.
*Diameter.*—3 mm.
*Fall color.*—SP.
*Length of petiole compared to middle vein.*—Approximately 1:1 ratio.
*Density of prostrate hairs on petiole.*—Absent.
*Density of erect hairs on petiole.*—Absent.
*Shape of base of petiole sinus.*—Typical lyre.

FLOWERS

General:
*Date first bloom.*—September 11.
*Date full bloom.*—September 18.
*Date last bloom.*—September 25.
*Flower sex.*—Hermaphrodite (perfect flower).
*Position of first flowering nodes.*—4.8.
*Number of inflorescences per shoot.*—1.8.
*Pedicel length.*—2-3 mm.
*Calyptra color.*—Green (PMS 363).
*Ovary length.*—1-1.5 mm.
*Ovary width.*—1-1.5 mm.
*Ovary color.*—Green (PMS 363).
*Filament length.*—1.4 mm.
*Filament color.*—Light green.
*Anther length.*—0.6 mm.
*Anther color.*—Yellowish green (PMS 365).
*Stamen color.*—Greenish yellow (PMS 367).
*Stamen number.*—5.
*Pistil number.*—One, consisting of 5 carpels.
*Pistil length.*—1.8 mm.
*Pistil color.*—Green.
*Petal color.*—Green.
*Sepal number.*—5.
*Sepal color.*—Green (PMS 363).
*Pollen color.*—Yellow green (PMS 372).
*Individual flower dimensions.*—2.5 mm Length and 2 mm Width.
*Number of flowers per cluster.*—Average 248.
*Flower fragrance.*—Neutral.
*Cluster shape.*—Large and straggly.
*Mature cluster length.*—29 cm.
*Mature cluster width.*—27 cm.
*Mature cluster weight.*—1302 g.

FRUIT

General:
*Date ripe.*—In Southern Hemisphere: Late November to beginning January (in an early production area).
*Berry weight.*—4.95 gm.
*Berry diameter at equator.*—2.0 cm.
*Berry diameter at base.*—0.3 cm.
*Berry diameter at apex.*—0.0 cm (round berry).
*Berry length.*—2.2 cm.
*Berry shape.*—Globose to round elliptic.
*Berry color.*—Red (PMS 505) .
*Berry flesh color.*—Translucent white (PMS 5005).
*Skin thickness.*—0.2 mm.
*Total acids.*—6.5 g/l.
*Berries/cluster.*—300 plus.
*Cluster/vine.*—48 for a 3 m×1.8 m vine spacing.
*Cluster/shoot.*—1.8.
*Brush length.*—0.4-0.5 cm.
*Average peduncle length.*—5-6 cm.
*Pedicel length.*—7-10 mm.
*Pedicel diameter.*—2.5 mm.
*Pedicel color.*—Green (PMS 363).
*Pedicel texture.*—Rough due to lenticels.

*Pedicel lenticels*.—Many.
*Pedicel arrangement*.—2-3 in grouping.
*Ease of detachment from pedicel*.—Not easy.
*Sugar content of must*.—16-18° B.
*Acid content of must*.—6.5 g/l .
*Juiciness of flesh*.—Juicy.
*Firmness of flesh*.—Very firm.
*Flavor*.—Neutral but sweet.
*Eating quality*.—Good.
*Shipping and handling qualities*.—Excellent, a very strong variety.
*Keeping quality*.—Outstanding post harvest shelf-life.
*Winter hardiness*.—Good.
*Wood ripening*.—Good.
*Wine quality*.—Not applicable.

SEEDS

General:

*Presence of seeds*.—Absent to very small rudimentary (non-lignified).
*Seed color*.—Light green PMS 367 (not lignified).
*Productivity*.—Highly productive.

BIOTIC STRESS SUSCEPTIBILITY

Susceptibility:

*Susceptibility to powdery mildew* (*Uncinula necator*).—Normal.
*Susceptibility to downy mildew* (*Plasmopara viticola*).—Normal.
*Susceptibility to crown gall* (*Agrobacteriutumefaciens*).—Normal.
*Susceptibility to noble rot* (*Botrytis cinerea*).—Resistant.
*Susceptibility to anthracnose* (*Elsinoe ampelina*).—Normal.
*Susceptibility to dieback* (*Eutypa lata*).—Normal.
*Susceptibility to cane and leaf spot* (*Phomopsis viticola*) .—Normal.

SECONDARY BUNCHES

Small secondary bunches were observed at approximately 1 secondary bunch per 3 shoots.

COMPARISON BETWEEN PARENTAL AND COMMERCIAL CULTIVARS

| Characteristics | Red Globe | Flame Seedless | Tawny Seedless |
|---|---|---|---|
| Plant Vigour | Average | Strong | Very strong |
| Fertility | Average | Fertile | Very fertile |
| Time of harvest | Mid season | Early | Early - mid season |
| Resistance to rain | Good | Sensitive | Very resistant |
| Seedlessness | Seeded | Seedless | Seedless |
| Bunch size | Very large | Average | Very large |
| Bunch shape | Loose/straggly | Slightly compact | Loose/straggly |
| Eveness of berry size | Even | slightly uneven | very even |
| Berry size (natural) | 24 mm | 16 mm | 18 mm |
| Berry attachment | Good | Some shatter | Very good |
| Crispiness | Soft flesh | Crispy flesh | Very crispy flesh |
| Post-harvest shelf life | Good | Poor | Excellent |

The invention claimed is:

1. A new and distinct variety of grape plant named 'Tawny Seedless', substantially as illustrated and described herein.

* * * * *